United States Patent
Lee et al.

(10) Patent No.: US 9,289,630 B2
(45) Date of Patent: Mar. 22, 2016

(54) HAIR CONDITIONING COMPOSITION COMPRISING CATIONIC SURFACTANT SYSTEM, DIRECT DYE, AND NONIONIC THICKENER

(75) Inventors: Yungi Lee, Kobe (JP); Nobuaki Uehara, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 23 days.

(21) Appl. No.: 12/915,209

(22) Filed: Oct. 29, 2010

(65) Prior Publication Data

US 2011/0104094 A1   May 5, 2011

Related U.S. Application Data

(60) Provisional application No. 61/256,080, filed on Oct. 29, 2009.

(51) Int. Cl.
| | |
|---|---|
| *A61Q 5/12* | (2006.01) |
| *A61K 8/34* | (2006.01) |
| *A61K 8/41* | (2006.01) |
| *A61K 8/73* | (2006.01) |
| *A61Q 5/06* | (2006.01) |
| *A61K 8/42* | (2006.01) |

(52) U.S. Cl.
CPC . *A61Q 5/12* (2013.01); *A61K 8/342* (2013.01); *A61K 8/416* (2013.01); *A61K 8/42* (2013.01); *A61K 8/73* (2013.01); *A61K 8/731* (2013.01); *A61Q 5/065* (2013.01); *A61K 2800/432* (2013.01); *A61K 2800/5422* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 4,678,475 | A | 7/1987 | Hoshowski |
| 5,948,124 | A | 9/1999 | Grit |
| 6,129,770 | A * | 10/2000 | Deutz et al. ........................ 8/406 |
| 6,645,480 | B2 | 11/2003 | Giles et al. |
| 7,361,198 | B2 | 4/2008 | Goettel et al. |
| 7,918,901 | B2 | 4/2011 | Runglertkriangkrai |
| 2004/0158939 | A1 | 8/2004 | Wells |
| 2004/0234491 | A1 * | 11/2004 | Brautigam et al. ........ 424/70.28 |
| 2006/0096041 | A1 | 5/2006 | Molenda |
| 2006/0130247 | A1 | 6/2006 | Molenda |
| 2007/0010408 | A1 * | 1/2007 | Uehara ......................... 510/119 |
| 2009/0185994 | A1 | 7/2009 | Bistram |
| 2010/0150858 | A1 * | 6/2010 | Runglertkriangkrai .... 424/70.28 |
| 2011/0104094 | A1 | 5/2011 | Lee |

FOREIGN PATENT DOCUMENTS

| | | |
|---|---|---|
| DE | 19641841 C2 | 5/1999 |
| DE | 29903100 U1 | 9/2000 |
| EP | 0819422 A1 | 1/1998 |
| EP | 2018842 A1 | 1/2009 |
| EP | 1502578 B1 | 4/2009 |
| JP | 62-277313 A | 12/1987 |
| JP | 05-043438 * | 2/1993 |
| JP | 5043438 A2 | 2/1993 |
| JP | 5194161 A2 | 8/1993 |
| JP | 6271434 A2 | 9/1994 |
| JP | 10-072327 A | 9/1999 |
| JP | 2000-86439 A | 3/2000 |
| JP | 2000128750 A2 | 5/2000 |
| JP | 2001294519 A | 10/2001 |
| JP | 2002-327193 A | 11/2002 |
| JP | 2003-516956 A | 5/2003 |
| JP | 2003-160446 A | 6/2003 |
| JP | 2004059565 A2 | 2/2004 |
| JP | 2005-206573 A | 8/2005 |
| WO | WO2005/051889 A1 | 6/2005 |
| WO | WO2008/152595 A2 | 12/2008 |
| WO | WO2010068400 A2 | 6/2010 |

OTHER PUBLICATIONS

International Search Report; PCT/US2010/054176; Mailing Date May 7, 2013; 16 pages.

* cited by examiner

*Primary Examiner* — Jyothsna Venkat
(74) *Attorney, Agent, or Firm* — Linda M. Sivik

(57) ABSTRACT

Disclosed is a hair conditioning composition comprising: a cationic surfactant system comprising a mono-long alkyl cationic surfactant and a di-long alkyl cationic surfactant; a high melting point fatty compound; a direct dye; a nonionic thickening polymer having a viscosity of the aqueous solution with 2% of the nonionic thickening polymer being from about 1,000 to about 300,000 m·Pa, at 25° C.; and an aqueous carrier; wherein the composition has a pH of above 4.5 to about 9.0. The composition of the present invention provides improved product stability and color stability, while providing conditioning benefits and coloring benefits.

1 Claim, No Drawings

HAIR CONDITIONING COMPOSITION COMPRISING CATIONIC SURFACTANT SYSTEM, DIRECT DYE, AND NONIONIC THICKENER

CROSS REFERENCE TO RELATED APPLICATIONS

This application claims the benefit of U.S. Provisional Application No. 61/256,080 filed on Oct. 29, 2009.

FIELD OF THE INVENTION

The present invention relates to a hair conditioning composition comprising: a cationic surfactant system comprising a mono-long alkyl cationic surfactant and a di-long alkyl cationic surfactant; a high melting point fatty compound; a direct dye; a nonionic thickening polymer; and an aqueous carrier; wherein the composition has a pH of from about 4.5 to about 9.0. The composition of the present invention provides improved product stability and/or color stability, while providing conditioning benefits and coloring benefits.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits. For example, some cationic surfactants, when used together with some high melting point fatty compounds, are believed to provide a gel matrix which is suitable for providing a variety of conditioning benefits such as slippery feel during the application to wet hair and softness and moisturized feel on dry hair.

There is a need for hair conditioning compositions which provide coloring benefits while providing conditioning benefits. Such coloring benefit is, for example, at least one of the followings: coloring to non-colored hair, color enhancing of colored hair, preventing color fade of colored hair and grey blending.

A variety of attempts has been made for providing both hair coloring and hair conditioning benefits. For example, Japanese Patent Application Laid-open No. H5-43438 relates to a coloring hair treatment containing two types of cationic surfactants, an acidic dye, and the treatment having a pH value of from 1.5 to 4.5. Japanese Patent Application Laid-open No. H5-43438 discloses a coloring hair treatment composition in Example 3 comprising 0.3% of Behentrimonium Chloride, 0.1% of Cetyltrimonium Chloride, 0.1% of Distearyldimonium Chloride, 10% of Behenyl alcohol, and 0.05% of an acidic dye, and the composition having a pH value of 2.2.

There is a need for conditioners containing direct dyes, especially when containing nonionic and/or cationic dyes, to be kept at a higher pH than conditioners without dyes, for providing desirable color shade to hair in a log term period. At a higher pH, due to the reduced decomposition of such dyes, the conditioners can provide better long term stability of the color performance. There may also be a need for conditioners containing direct dyes to be kept at a higher pH than conditioners without dyes, for providing desirable product color from the dyes.

However, it has been surprisingly found that, at a higher pH, some compositions drive product instability such as phase separation and/or color instability which may result in undesirable hair color. It has been also found that such product instability at a higher pH can be observed more in compositions containing a cationic surfactant system comprising mono-long alkyl cationic surfactant and di-long alkyl cationic surfactant, compared to compositions containing mono-long alkyl cationic surfactants and being substantially free of di-long alkyl cationic surfactant.

Based on the foregoing, there remains a need for hair conditioning compositions, especially in compositions containing a cationic surfactant system comprising mono-long alkyl cationic surfactant and di-long alkyl cationic surfactant, which provide conditioning benefits and coloring benefits at a higher pH, together with improved product stability and/or improved color stability.

None of the existing art provides all of the advantages and benefits of the present invention.

SUMMARY OF THE INVENTION

The present invention is directed to a hair conditioning composition comprising by weight:
(a) from about 0.2% to about 10% of a cationic surfactant system comprising a mono-long alkyl cationic surfactant and a di-long alkyl cationic surfactant;
(b) from about 1% to about 15% of a high melting point fatty compound;
(c) from about 0.00005% to about 0.5% of a direct dye; and
(d) from about 0.0001% to about 10% of a nonionic thickening polymer having a viscosity of the aqueous solution with 2% of the nonionic thickening polymer being from about 1,000 to about 300,000 m·Pa, at 25° C.;
(e) an aqueous carrier,
wherein the composition has a pH of above 4.5 to about 9.0.

The conditioning compositions of the present invention provide improved product stability and/or improved color stability, while providing conditioning benefits and coloring benefits.

These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Composition

The composition of the present invention has a pH of above 4.5 (excluding 4.5) to about 9.0, preferably from about 5.0 to about 8.5, still more preferably from about 5.5. to about 8.0, in view of appropriate shade and long-term color stability. The pH can be adjusted by buffer agents, for example, alkanoamine, such as mono-, di- and tri-ethanolamine, sodium hydroxide, potassium hydroxide, alkaline carbonate, such as sodium carbonate, phosphate buffer, such as mono- and di-sodium phosphate, mono- and di-photassium phosphate, borax, such as sodium borate, sodium tetraborate and disodium tetraborate etc.

Preferably, the composition of the present invention is substantially free of anionic surfactants and anionic polymers, in view of compatibility with cationic surfactants, and stability of the gel matrix when formed by cationic surfactants and high melting point fatty compounds. In the present invention, "the composition being substantially free of anionic surfactants and anionic polymers" means that: the composition is free of anionic surfactants and anionic polymers; or, if the composition contains anionic surfactants and anionic polymers, the level of such anionic surfactants and anionic polymers is very low. In the present invention, a total level of such anionic surfactants and anionic polymers, if included, preferably 1% or less, more preferably 0.5% or less, still more preferably 0.1% or less by weight of the composition. Most preferably, the total level of such anionic surfactants and anionic polymers is 0% by weight of the composition.

Cationic Surfactant System

The composition of the present invention comprises a cationic surfactant system. The cationic surfactant is included in the composition at a level by weight of from about 0.2% to about 10%, preferably from about 0.3% to about 8%, more preferably from about 0.4% to about 5%, in view of providing conditioning benefits and improved coloring benefits together with high melting point fatty compounds and direct dyes.

The cationic surfactant system of the present invention comprises a mono-long alkyl cationic surfactant and a di-long alkyl cationic surfactant. In the system, it is preferred that the weight ratio of the di-long alkyl cationic surfactant to the mono-long alkyl cationic surfactant is within the range of from about 1:1 to about 1:20, more preferably from about 1:1 to about 1:15, still more preferably from about 1:1 to about 1:10, in view of providing conditioning benefits and improved coloring benefits.

Such mono-long alkyl cationic surfactants include, for example, mono-long alkyl quaternary ammonium salts and mono-long alkyl amines. Mono-long alkyl amines include, for example, mono-long alkyl amidoamines and salts thereof. Among those mono-long alkyl cationic surfactants, the following (i) and (ii) may be preferred in view of providing improved color benefits, and the following (i) may be more preferred in view of providing improved conditioning/color benefits at the same time: (i) salts of mono-long alkyl quaternized ammoniums and anions wherein the anions are selected from the group consisting of C1-C4 alkyl sulfate, and mixtures thereof; and (ii) salts of mono-long alkyl amines wherein the mono-long alkyl group has 20 to about 24 carbon atoms. Among a variety of the cationic surfactant systems, the following systems may be preferred: the system comprising mono-long alkyl cationic surfactants selected from the group consisting of behenyl trimethyl ammonium methyl sulfate, behenyl trimethyl ammonium ethyl sulfate, and mixtures thereof, and di-long alkyl cationic surfactants selected from the group consisting of dicetyl dimethyl ammonium chloride, distearyl dimethyl ammonium chloride, and mixtures thereof.

The compounds, which can be used in the cationic surfactant system of the present invention, are explained below in detail.

Mono-Long Alkyl Quaternized Ammonium Salt Cationic Surfactant

One of the preferred cationic surfactants of the present invention is a salt of a mono-long alkyl quaternized ammonium and an anion, wherein the anion is selected from the group consisting of halides such as chloride and bromide, C1-C4 alkyl sulfate such as methosulfate and ethosulfate, and mixtures thereof.

The mono-long alkyl quaternized ammonium salts useful herein are those having the formula (I):

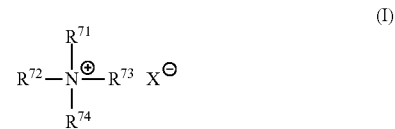

wherein one of $R^{71}$, $R^{72}$, $R^{73}$ and $R^{74}$ is selected from an aliphatic group of from 16 to 40 carbon atoms or an aromatic, alkoxy, polyoxyalkylene, alkylamido, hydroxyalkyl, aryl or alkylaryl group having up to about 40 carbon atoms; the remainder of $R^{71}$, $R^{72}$, $R^{73}$ and $R^{74}$ are independently selected from an aliphatic group of from 1 to about 8 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{72}$, $R^{73}$ and $R^{74}$ is selected from an alkyl group of from 16 to 40 carbon atoms, more preferably from 18 to 26 carbon atoms, still more preferably from 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof. It is believed that mono-long alkyl quaternized ammonium salts can provide improved hydrophobicity and smooth feel on dry hair, compared to amine or amine salt cationic surfactants.

Among them, more preferred cationic surfactants are those having a longer alkyl group, i.e., C18-22 alkyl group. Such cationic surfactants include, for example, behenyl trimethyl ammonium chloride, methyl sulfate or ethyl sulfate, and stearyl trimethyl ammonium chloride, methyl sulfate or ethyl sulfate. More preferred are behenyl trimethyl ammonium methyl sulfate or ethyl sulfate and stearyl trimethyl ammonium methyl sulfate or ethyl sulfate, and still more preferred is behenyl trimethyl ammonium methyl sulfate or ethyl sulfate. It is believed that; cationic surfactants having a longer alkyl group provide improved smoothness and soft feeling on wet and dry hair, compared to cationic surfactant having a shorter alkyl group. It is also believed that such cationic surfactants can provide reduced irritation, compared to cationic surfactants having a shorter alkyl group. It is further believed that; behenyl trimethyl ammonium methyl sulfate with a di-alkyl quaternary ammonium salt can provide improved coloring benefits, while providing conditioning benefits, compared to behenyltrimethylammonium chloride with a di-alkyl quaternary ammonium salt.

Mono-Long Alkyl Amine Cationic Surfactant

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Di-Long Alkyl Quaternized Ammonium Salt

Di-long alkyl quaternized ammonium salts useful herein are those having the formula (II):

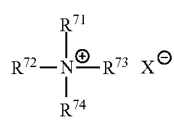

(II)

wherein two of $R^{71}$, $R^{72}$, $R^{73}$ and $R^{74}$ is selected from an aliphatic group of from 16 to 40 carbon atoms or an aromatic, alkoxy, polyoxyalkylene, alkylamido, hydroxyalkyl, aryl or alkylaryl group having up to about 40 carbon atoms; the remainder of $R^{71}$, $R^{72}$, $R^{73}$ and $R^{74}$ are independently selected from an aliphatic group of from 1 to about 8 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{72}$, $R^{73}$ and $R^{74}$ is selected from an alkyl group of from 16 to 40 carbon atoms, more preferably from 16 to 26 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof. Preferably, the anion is selected from the group consisting of halides such as chloride and mixtures thereof.

Such di-long alkyl quaternized ammonium salts useful herein include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The composition of the present invention comprises a high melting point fatty compound. The high melting point fatty compound is included in the composition at a level of from about 1% to about 15%, preferably from about 3% to about 10%, more preferably from about 5% to about 8% by weight of the composition, in view of providing conditioning benefits such as slippery feel during the application to wet hair, softness and moisturized feel on dry hair.

The high melting point fatty compound useful herein have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Direct Dye

The composition of the present invention comprises a direct dye. The direct dye is included in the composition at a level of from about 0.00005% to about 15.0%, preferably from about 0.0001% to about 10.0%, more preferably from about 0.001% to about 5.0% by weight of the composition, in view of providing color benefit without changing original hair color tone, and minimizing the staining during application.

The direct dyes are those which are also called as non-oxidative dyes. The direct dyes useful herein include, for example: nonionic dyes such as nitro dyes, azo dyes, and anthraquinone dyes; cationic dyes such as basic dyes; and anionic dyes such as acidic dyes. It is known that some azo dyes and anthraquinone dyes can be classified as cationic dyes or anionic dyes, when they have cationic or anionic substitutions. The dye can be used alone or in combination with other dyes, according to target color of hair to which the composition is applied.

Preferably, the direct dyes useful herein are nonionic direct dyes, cationic direct dyes, and mixtures thereof, in view of compatibility with cationic surfactants. Anionic dyes, when used, are preferably combined with nonionic direct dyes and/or cationic direct dyes.

The technology of the present invention is suitable for nonionic direct dyes, especially for nonionic nitrobenzene derivatives. Such nitrobenzene derivatives include, for example, 4-hydroxypropylamino-3-nitrophenol, 1-amino-5-chloro-4-[(2,3-dihydroxypropyl)amino]-2-nitrobenzene (HC Red No. 10), and 5-chloro-1,4-[di-(2,3-dihydroxypropyl)amino]-2-nitrobenzene (HC Red No. 11). The technology of the present invention is especially suitable for 4-hydroxypropylamino-3-nitrophenol.

Nonionic nitro dyes useful herein include, for example, 1,4-bis-[(2-hydroxyethyl)amino]-2-nitrobenzene, 1-(2-hydroxyethyl)amino-2-nitro-4-[di-(2-hydroxyethyl)amino] benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 1-[(2,3-dihydroxypropyl)amino]-4-[methyl-(2-hydroxyethyl) amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di-(2-hydroxyethyl)amino]-2-nitrobenzene (HC Violet No. 2), 1-amino-4-[(2-hydroxyethyl)amino]-2-nitrobenzene (HC Red No. 7), 2-amino-4,6-dinitrophenol, 1,4-diamino-2-nitrobenzene (CI76070), 4-amino-2-nitrodiphenylamine (HC Red No. 1), 1-amino-4-[di-(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-2-nitro-1-((prop-2-en-1-yl)amino)benzene, 4-amino-3-nitrophenol, 4-[(2-hydroxyethyl)amino]-3-nitrophenol, 4-[(2-nitrophenyl)amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di-(2,3-dihydroxypropyl)amino] -2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl) amino]benzoic acid, 2-chloro-6-ethylamino-4-nitrophenol, 2-amino-6-chloro-4-nitrophenol, 4-[(3-hydroxypropyl) amino]-3-nitrophenol, 2,5-diamino-6-nitropyridine, 3-amino-6-(methylamino)-2-nitropyridine, 1,2,3,4-tetrahydro-6-nitroquinoxaline, 7-amino-3,4-dihydro-6-nitro-2H-1, 4-benzoxazine (HC Red No. 14), 1,2-diamino-4-nitrobenzene (CI76020), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluoro-methylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), and 2,4-dinitro-1-hydroxynaphthalene.

Other nonionic direct dyes useful herein include, for example, 1,4-di-[(2,3-dihydroxypropyl)amino]-9,10-anthraquinone, 1,4-di-[(2-hydroxyethyl)amino] -9,10-anthraquinone (CI61545, Disperse Blue 23), 1-amino-4-hydroxy-9,10-anthraquinone (CI60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-dioxo-3,5,6,8-tetrahydroxy-2-anthracenecarboxylic acid (CI75470, Natural Red 4), 1-[(3-aminopropyl) amino]-9,10-anthraquinone (HC Red No. 8), 1,4-diamino-9, 10-anthraquinone (CI61100, Disperse Violet No. 1), 1-amino-4-(methylamino)-9,10-anthraquinone (CI61105, Disperse Violet No. 4, Solvent Violet No. 12), N-(6-((3-chloro-4-(methylamino)phenyl)imino)-4-methyl-3-oxo-1,4-cyclohexadien-1-yl)urea (HC Red No. 9), 2-((4-(di-(2-hydroxyethyl)amino)phenyl)amino)-5-((2-hydroxyethyl) amino)-2,5-cyclohexadien-1,4-dione (HC Green No. 1), 2-hydroxy-1,4-naphthoquinone (CI75480, Natural Orange No. 6), 1,2-dihydro-2-(1,3-dihydro-3-oxo-2H-indol-2-ylidene)-3H-indol-3-one (CI73000), 1,3-bis-(dicyanomethylidene)indane, 1-[di-(2-hydroxyethyl)amino]-3-methyl-4-[(4-nitrophenyl)azo]benzene (CI11210, Disperse Red No. 17), 1-[di-(2-hydroxyethyl)amino]-4-[(4-nitrophenyl)azo] benzene, (Disperse Black No. 9), 4-[(4-aminophenyl)azo]-1-[di-(2-hydroxyethyl)amino]-3-methylbenzene (HC Yellow No. 7), 2,6-diamino-3-[(pyridin-3-yl)azo]-pyridine and 2-((4-(ethyl-(2-hydroxyethyl)amino)-2-methylphenyl)azo)-5-nitro-1,3-thiazole (CI111935; Disperse Blue No. 106).

Cationic basic dye useful herein includes, for example, di-[4-(diethylamino)phenyl][4-(ethylamino)naphthyl]carbenium chloride (CI42595; Basic Blue No. 7), di-[4-(dimethylamino)phenyl][4-(phenylamino)naphthyl]carbenium chloride (CI44045; Basic Blue No. 26), Basic Blue No. 77, 8-amino-2-bromo-5-hydroxy-4-imino-6-[(3-(trimethylammonio)-phenyl)amino]-1(4H)-naphthalenone chloride (CI56059; Basic Blue No. 99), tri-(4-amino-3-methylphenyl) carbenium chloride (CI42520; Basic Violet No. 2), di-(4-aminophenyl)(4-amino-3-methylphenyl)carbenium chloride (CI42510; Basic Violet No. 14), 1-[(4-aminophenyl)azo]-7-(trimethylammonio)-2-naphthol chloride (CI12250; Basic Brown No. 16), 3-[(4-amino-2,5-dimethoxyphenyl)azo]-N, N,N-trimethylbenzolaminium chloride (CI112605, Basic Orange No. 69), 1-[(4-amino-2-nitrophenyl)azo]-7-(trimethylammonio)-2-naphthol chloride (Basic Brown No. 17), 2-((4-aminophenyl)azo)-1,3-dimethyl-1H-imidazol-3-ium chloride (Basic Orange No. 31), 3,7-diamino-2,8-dimethyl-5-phenylphenazinium chloride (CI50240; Basic Red No. 2), 1,4-dimethyl-5-[(4-(dimethylamino)phenyl)azo]-1,2,4-triazolium chloride (CI11055; Basic Red No. 22), 1,3-dimethyl-2-((4-dimethylamino)phenyl)azo-1H-imidazol-3-ium chloride (Basic Red No. 51), 2-hydroxy-1-[(2-methoxyphenyl) azo]-7-(trimethylammonio)naphthalene chloride (CI12245; Basic Red No. 76), 3-methyl-1-phenyl-4-[(3-(trimethylammonio)phenyl)azo]pyrazol-5-one chloride (CI12719; Basic Yellow No. 57), and 1-methyl-4-((methylphenyl-hydrazono) methyl)pyridinium methyl sulfate (Basic Yellow No. 87).

Other cationic direct dyes useful herein include, for example, Benzenamine, 4-[(2,6-Dichlorophenyl)(4-Imino-3, 5-Dimethyl-2,5-Cyclohexadien-1-ylidene)Methyl]-2,6-Dimethyl-, Phosphate) (HC Blue No. 15), 1-(2-morpholiniumpropylamino)-4-hydroxy-9,10-anthraquinone methyl sulfate, and 1-[(3-(dimethylpropylaminium)propyl)amino]-4-(methylamino)-9,10-anthraquinone chloride.

Anionic direct dyes useful herein include, for example, disodium bis[4-(N-ethyl-N-3-sulfonatophenylmethyl)aminophenyl]phenylmethylium (INCI name: Acid Blue 9), Benzenesulfonic acid, 2-[(9,10-Dihydro-4-hydroxy-9,10-Dioxo-1-anthracenyl)amino]-5-methyl-, monosodium salt (INCI name: Ext. Violet 2). p-((2-Hydroxy-1-naphthyl)azo)benzenesulfonic acid sodium salt (INCI name: Orange 4), 2,2'-(1, 4-Anthraquinonylenediimino)bis(5-methylbenzenesulfonic acid) disodium salt (INCI name: ACID GREEN 25), Acides 2-(2-quinoleyl) 1,3-indanedione mono, di, trisulfoniques, sodium salt (INCI name: Yellow 10), 5-amino-4-hydroxy-30 (phenylazo)-2,7-naphthalenesulfonic acid, disodium salt (INCI name: Acid Red 33).

Nonionic Thickening Polymer

The conditioning composition of the present invention comprises a nonionic thickening polymer. It is believed that nonionic thickening polymer, compared to anionic and cationic thickening polymers, provides better compatibility with gel matrix formed by cationic surfactants, high melting point fatty compounds, and aqueous carrier, and thus provides better thickening effect, product stability, and/or better hair feel.

The nonionic thickening polymer is included in the composition at a level of from about 0.0001% to about 10%, preferably from about 0.005% to about 5%, more preferably from about 0.001% to about 3%, still more preferably from about 0.01% to about 1% by weight of the composition, in view of providing thickening benefit, while avoiding any undesirable hair feel such as stickiness and roughness.

The nonionic thickening polymers useful herein are those which are water soluble and have an appropriate viscosity when 2% of nonionic polymer is dissolved in aqueous solution. The suitable viscosity of the aqueous solution with 2% nonionic polymer is from about 1,000 to about 300,000 m·Pa, preferably from about 5,000 to about 250,000 m·Pa, more preferably from about 10,000 to about 150,000 m·Pa measured at 25° C. using Brookfield viscometer.

A variety of nonionic thickening polymers can be used in the compositions of the present invention. Nonionic thickening polymers useful herein include, for example, a nonionic cellulose and its derivatives such as cellulose ethers including hydroxyethylcellulose and hydroxypropylcellulose, hydrophobically modified cellulose ethers such as cetyl hydroxyethylcellulose which is supplied, for example, by Hercules with a tradename Polysurf 67; nonionic guar polymers such as Guar Gum 2-hydroxypropyl ether which is supplied, for example, by Rhodia with a tradename Jaguar HP-105; nonionic crosslinked polymers; and polyethylacrylate, and polyacrylamide. Among a variety of nonionic thickening polymers, nonionic polysaccharides such as nonionic cellulose derivatives may be preferred.

Aqueous Carrier

The conditioning composition of the present invention comprises an aqueous carrier. The level and species of the carrier are selected according to the compatibility with other components, and other desired characteristic of the product. Generally, the compositions of the present invention comprise from about 20% to about 99%, preferably from about 30% to about 95%, and more preferably from about 80% to about 95% water.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product.

Gel Matrix

Preferably, the above cationic surfactants, together with high melting point fatty compounds and an aqueous carrier, form a gel matrix in the composition of the present invention.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6, more preferably form about 1:1 to about 1:4.

Silicone Compound

Preferably, the compositions of the present invention contain a silicone compound. It is believed that the silicone compound can provide smoothness and softness on dry hair. The silicone compounds herein can be used at levels by weight of the composition of preferably from about 0.1% to about 20%, more preferably from about 0.15% to about 10%, still more preferably from about 0.2% to about 8%.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferably, the silicone compounds have an average particle size of from about 1 microns to about 50 microns, in the composition.

Preferably, silicone compounds useful herein include amino substituted materials. Preferred aminosilicones include, for example, those which conform to the general formula (III):

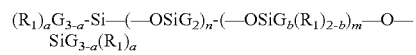

wherein G is hydrogen, phenyl, hydroxy, or $C_1$-$C_8$ alkyl, preferably methyl; a is an integer having a value from 1 to 3, preferably 1; b is 0, 1 or 2, preferably 1; n is a number from 1 to 2,000, preferably from 100 to 2,000, more preferably from 300 to 1,800; m is an integer from 0 to 1,999, preferably from 0 to 10, more preferably 0; $R_1$ is a monovalent radical conforming to the general formula $CqH_{2q}L$, wherein q is an integer having a value from 2 to 8 and L is selected from the following groups: —$N(R_2)CH_2$—$CH_2$—$N(R_2)_2$; —$N(R_2)_2$; —$N(R_2)_3A^-$; —$N(R_2)CH_2$—$CH_2$—$NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

One highly preferred amino silicones are those corresponding to formula (III) wherein m=0, a=1, q=3, G=methyl, n is preferably from about 1500 to about 1700, more preferably 1600; and L is —$N(CH_3)_2$ or —$NH_2$, more preferably —$NH_2$. Another highly preferred amino silicones are those corresponding to formula (III) wherein m=0, a=1, q=3, G=methyl, n is preferably from about 400 to about 600, more preferably about 500; and L is —$N(CH_3)_2$ or —$NH_2$, more preferably —$NH_2$. Such highly preferred amino silicones can be called as terminal aminosilicones, as one or both ends of the silicone chain are terminated by nitrogen containing group. It is believed that, such terminal aminosilicone can provide balanced benefit between conditioning benefits and clean feel, compared to other silicones such as graft aminosilicones and silicones having no amino substitution.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

The other silicone compounds useful herein include polyalkyl or polyaryl siloxanes with the following structure:

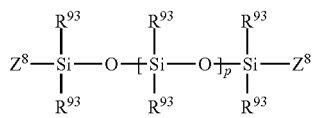

wherein $R^{93}$ is alkyl or aryl, and p is an integer from about 7 to about 8,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The other silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

The silicone compounds may further be incorporated in the present composition in the form of an emulsion, wherein the emulsion is made by mechanical mixing, or in the stage of synthesis through emulsion polymerization, with or without the aid of a surfactant selected from anionic surfactants, nonionic surfactants, cationic surfactants, and mixtures thereof.

Among the variety of the silicone compounds, a combination of graft aminosilicones and silicone resins may also be preferred to provide durable conditioning and chronic/long lasting color protection benefit. Such durable conditioning and chronic/long lasting color protection benefits are, for example, at least one of the followings: maintaining good sensory feel long period after coloring hair, preventing color fading of colored hair or minimizing/slowing down color lost until next coloring hair. Such combination of graft aminosilicones and silicone resins may be preferably used in combination with the above aminosilicone of the formula (III). Such graft aminosilicones include, for example, commercially available fluids under the trade names ADM1100 from Wacker Silicones, AP6087, DC8803 from Dow Corning Corporation, and TSF 4707 from GE Bayer Silicones. Such silicone resins include, for example, those commercially available as SR1000 available from GE Bayer Silicones and Wacker 803 from Wacker Silicones.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: cationic conditioning polymers including, for example, cationic celluloses such as polyquaternium-10, and cationic guar gums; low melting point oils having a melting point of less than 25° C. including, for example, unsaturated fatty alcohols such as oleyl alcohol and ester oils such as pentaerythritol ester oils; polyethylene glycols; other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and Phenoxyethanol; perfumes; sequestering agents, such as ethylenediamine tetra acetic acid and its salts; and ultraviolet and infrared screening and absorbing agents such as octyl salicylate, octyl methoxycinnamate, benzophenone-3 and benzophenone-4.

Product Forms

The conditioning compositions of the present invention can be in the form of rinse-off products or leave-on products, and can be formulated in a wide variety of product forms, including but not limited to creams, gels, emulsions, mousses and sprays.

as many variations thereof are possible without departing from the spirit and scope of the invention. Where applicable, ingredients are identified by chemical or CTFA name, or otherwise defined below.

[Compositions]

| Components | Ex. 1 | Ex. 2 | Ex. 3 | Ex. 4 | Ex. i | Ex. ii | Ex. iii | Ex. iv | Ex. v |
|---|---|---|---|---|---|---|---|---|---|
| Behenyl trimethyl ammonium methyl sulfate | 1.7 | 1.1 | — | — | 1.1 | 1.7 | 1.1 | 1.7 | 1.1 |
| Behenamidopropyl-dimethylamine | — | — | 2.5 | 2.5 | — | — | — | — | — |
| 1-glutamic acid | — | — | 0.7 | 0.7 | — | — | — | — | — |
| Behenyl trimethyl ammonium chloride | — | — | — | — | — | — | — | — | — |
| Dicetyl dimethyl ammonium chloride | 0.5 | 0.35 | — | — | 0.35 | 0.5 | 0.35 | 0.5 | 0.35 |
| Distearyl dimethyl ammonium chloride | — | — | 0.60 | 0.60 | — | — | — | — | — |
| Cetyl alcohol | 1.3 | 0.9 | 1.5 | 1.5 | 0.9 | 1.3 | 0.9 | 1.3 | 0.9 |
| Stearyl alcohol | 3.3 | 2.3 | 4.0 | 4.0 | 2.3 | 3.3 | 2.3 | 3.3 | 2.3 |
| Hydroxyethylcellulose-1 *1 | 0.1 | 0.1 | 0.025 | 0.025 | — | — | — | — | — |
| Hydroxyethylcellulose-2 *2 | — | — | — | — | 0.1 | — | — | — | — |
| Xanthan gum *3 | — | — | — | — | — | 0.1 | — | — | — |
| Aminosilicone-1 *4 | 0.5 | 0.5 | — | 0.5 | 0.5 | 0.5 | 0.5 | 0.5 | 0.5 |
| Dimethicone/Cyclomethicone *5 | — | — | 4.2 | — | — | — | — | — | — |
| Aminosilicone-2 *6 | — | — | — | 3.5 | — | — | — | — | — |
| MQ resin *7 | — | — | — | 0.0035 | — | — | — | — | — |
| Basic Brown 16 | — | — | 0.008 | 0.008 | — | — | — | — | — |
| HC Red No 10 & 11 | 0.07 | 0.07 | 0.006 | 0.006 | 0.07 | 0.07 | 0.07 | 0.07 | — |
| 4-hydroxypropylamino-3-nitrophenol | 0.07 | 0.07 | 0.005 | 0.005 | 0.07 | 0.07 | 0.07 | 0.07 | — |
| UV absorbers | — | — | 0.1 | 0.1 | — | — | — | — | — |
| Preservatives | 0.4 | 0.4 | 0.4 | 0.4 | 0.4 | 0.4 | 0.4 | 0.4 | 0.4 |
| Perfume | 0.4 | 0.4 | 0.4 | 0.4 | 0.4 | 0.4 | 0.4 | 0.4 | 0.4 |
| Panthenol | — | — | 0.03 | | | | | | |
| Panthenyl ethyl ether | — | — | 0.03 | | | | | | |
| Monoethanolamine | 0.1 | 0.1 | 0.1 | 0.1 | 0.1 | 0.1 | 0.1 | 0.1 | — |
| Potassium phosphate | 0.2 | 0.4 | 0.2 | 0.2 | 0.2 | 0.2 | 0.2 | 0.2 | — |
| Deionized Water | | | | q.s. to 100% | | | | | |
| pH | 6.5 | 6.5 | 6.5 | 6.5 | 6.5 | 6.5 | 6.5 | 6.5 | 4.3 |

Definitions of Components

*1 Hydroxyethylcellulose-1: Natrosol 250 HHR, Hercules, having a viscosity of 100,000 m · Pa (2% aqueous solution) at 25° C. using Brookfield viscometer
*2 Hydroxyethylcellulose-2: Natrosol 250 GR, Hercules, having a viscosity of 350 m · Pa (2% aqueous solution) at 25° C. using Brookfield viscometer
*3 Xanthan gum: Keltrol, CPKelco (Anionic thickening polymer)
*4 Aminosilicone: Terminal aminosilicone which is available from GE having a viscosity 10,000 mPa · s, and having following formula (III): $(R_1)_a G_{3-a}-Si-(-OSiG_2)_n-O-SiG_{3-a}(R_1)_a$ (III) wherein G is methyl; a is an integer of 1; n is a number from about 400 to about 600; $R_1$ is a monovalent radical conforming to the general formula $CqH_{2q}L$, wherein q is an integer of 3 and L is $-NH_2$
*5 Dimethicone/Cyclomethicone: a blend dimethicone having a viscosity of 18,000,000 mPa · s and cyclopentasiloxane available from GE Toshiba
*6 Aminosilicone-2: ADM1100 from Wacker Silicones
*7 MQ resin: SR1000 (Polytrimethyl hydrosilylsilicate) from GE Silicones The conditioning composition of the present invention is especially suitable for rinse-off hair conditioner. Such compositions are preferably used by following steps:
(i) after shampooing hair, applying to the hair an effective amount of the conditioning compositions for conditioning the hair; and
(ii) then rinsing the hair.

EXAMPLES

The following examples further describe and demonstrate embodiments within the scope of the present invention. The examples are given solely for the purpose of illustration and are not to be construed as limitations of the present invention, Method of Preparation The conditioning compositions of "Ex. 1" through "Ex. 4" as shown above can be prepared by any conventional method well known in the art. They are suitably made as follows:

Cationic surfactants, high melting point fatty compounds and direct dyes are added to water with agitation, and heated to about 80° C. The mixture is cooled down to about 50° C. If included, silicone compounds, perfumes, preservatives are added to the mixture with agitation. Then the mixture is cooled down to room temperature.

Examples 1 through 4 are hair conditioning compositions of the present invention which are particularly useful for rinse-off use. The embodiments disclosed and represented by the previous "Ex. 1" through "Ex. 4" have many advantages. For example, they have improved product stability and color stability while providing conditioning benefits and color benefits. They are especially suitable for red or brown colored hair.

Product Stability

With respect to some of the above compositions, product stability is evaluated by the following method. Results of the evaluation are also shown below in Table 1.

Stability is Evaluated as Follows:
i) About 30 g of sample stored at 5° C. is taken in the centrifugation cell and is centrifuged under 15000 rpm for 1 h at 20° C. using a centrifuge instrument called Beckman Avanti HP-25 high performance centrifuge system.
ii) After centrifugation, % separated water to entire aqueous carrier amount in the formula is calculated by weighing separated water phase.

TABLE 1

|  | Ex. 1 | Ex. 2 | Ex. i | Ex. ii | Ex. iii | Ex. iv | Ex. v |
|---|---|---|---|---|---|---|---|
| Product stability | A | C | F | F | G | E | C |

A: Above 50% (excluding 50%) to 100% decrease of the amount of separated water, compared to Control
B: Above 10% (excluding 10%) to 50% decrease of the amount of separated water, compared to Control
C: Control or Equal to Control
D: Above 10% (excluding 10%) to 50% increase of the amount of separated water, compared to Control
E: Above 50% (excluding 50%) to 100% increase of the amount of separated water, compared to Control
F: Above 100% (excluding 100%) to 150% increase of the amount of separated water, compared to Control
G: Above 150% (excluding 150%) to 200% increase of the amount of separated water, compared to Control The composition of Ex. v, used herein as Control, has enough product stability as a commercial product. Product stability is shown by the amount of separated water. Increased amount of separated water is considered as decreased product stability.

Color Stability

With respect to the above compositions of Ex. 1 and Ex. iv, color stability is evaluated by the following method. Results of the evaluation are also shown below in Table 2.

Color Stability is Evaluated as Follows:
i) The sample is treated with the as-made composition and its aged composition which has been stored at 40° C. for 6 months as follows:
10 g of the composition is applied and evenly spread to the sample, then rinsed off from the sample. Then the sample is dried.
ii) After the treatments, the color of the treated hair samples with as-made composition (hereinafter Color N) and the aged composition (hereinafter Color T) is measured using an instrument called X-Rite SP64 Spectrophotometer.
iii) The L, a, b values for Color N and Color T are then compared to calculate the DE*94 ($k_L$=2, $k_C$=$k_H$=1) measurements, which is recommended for textile industry application.

TABLE 2

|  | Ex. 1 | Ex. iv |
|---|---|---|
| DE*94 | 0.65 | 3.74 |

DE*94 > 1.0: noticeable color change, according to David Hunter in IPA bulletin (January/February 2009), which describes that; "Known as Delta ECMC and Delta E-94, they allow anyone with the proper equipment to quantify color difference in a uniform manner based on how the human eye sees and interprets color. The formulas are designed so a unit of measure of "1 delta E" becomes the minimum level a trained human observer can perceive a color difference while also taking into consideration three important color attributes-hue, saturation, and lightness. These considerations provide important distinctions because our eyes will notice a shift in lightness or hue before perceiving a shift in color saturation."

The composition of Ex. 1 does not show noticeable color change, even after it has been stored for 6 months, while a similar composition of Ex. iv (which doesn't contain any nonionic thickening polymer) shows noticeable color change.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioning composition comprising by weight:
   (a) from about 0.3% to about 8% of a cationic surfactant system comprising a mono-long alkyl cationic surfactant and a di-long alkyl cationic surfactant wherein the mono-long alkyl cationic surfactant is selected from the group consisting of behenyl trimethyl ammonium methyl sulfate, behenyl trimethyl ammonium ethyl sulfate, and mixtures thereof, and wherein the di-long alkyl cationic surfactant is selected from the group consisting of dicetyl dimethyl ammonium chloride, distearyl dimethyl ammonium chloride, and mixtures thereof;
   (b) from about 3% to about 10% of a fatty alcohol selected from the group consisting of cetyl alcohol, stearyl alcohol, behenyl alcohol and mixtures thereof;
   (c) from about 0.00005% to about 0.5% of a direct dye; and
   (d) from about 0.01% to about 0.1% of a nonionic thickening polymer wherein the nonionic thickening polymer is selected from the group consisting of hydroxyethylcellulose, hydroxypropylcellulose, cetyl hydroxyethylcellulose and mixtures thereof;
   (e) an aqueous carrier, wherein the hair conditioning composition has a pH of from about 5.5 to about 8.0 wherein the weight ratio of the di-long alkyl cationic surfactant to the mono-long alkyl cationic surfactant in the cationic surfactant system is within the range of from 1:1 to 1:10, and wherein the hair conditioning composition is free of an anionic polymer and wherein the direct dye is non-ionic nitrobenzene derivatives and wherein the nonionic nitrobenzene derivatives is 4-hydroxypropylamino-3-nitrophenol wherein the hair conditioning composition comprises from about 0.1 to about 20% of a silicone compound and wherein the silicone compound is an aminosilicone compound, and wherein the hair conditioning composition is substantially free of anionic surfactants and is a rinse-off conditioning composition.

* * * * *